United States Patent [19]

Jasne et al.

[11] Patent Number: 5,077,415

[45] Date of Patent: Dec. 31, 1991

[54] DISUBSTITUTED AROMATIC DIANHYDRIDES

[75] Inventors: Stanley J. Jasne, Peekskill; Pasquale A. Falcigno, Yonkers, both of N.Y.

[73] Assignee: Ciba-Geigy Corporation, Ardsley, N.Y.

[21] Appl. No.: 467,622

[22] Filed: Jan. 19, 1990

[51] Int. Cl.$^5$ .......................................... C07D 307/89
[52] U.S. Cl. ..................................... 549/242; 549/241
[58] Field of Search ................................ 549/241, 242

[56] References Cited

U.S. PATENT DOCUMENTS

| | | | |
|---|---|---|---|
| 3,078,279 | 2/1963 | McCracken et al. | 549/241 |
| 4,329,291 | 5/1982 | Webb et al. | 549/241 |
| 4,329,292 | 5/1982 | Webb | 549/241 |
| 4,499,285 | 2/1985 | Evans | 549/241 |
| 4,578,166 | 3/1986 | Uno et al. | 549/241 |
| 4,625,037 | 11/1986 | Evans | 549/241 |
| 4,697,023 | 9/1987 | Schwartz et al. | 549/241 |
| 4,808,731 | 2/1989 | Berdahl et al. | 549/241 |
| 4,837,404 | 6/1989 | Schwartz | 549/241 |
| 4,868,316 | 9/1989 | Schwartz, Jr. | 569/241 |
| 4,870,194 | 9/1989 | Molinaro et al. | 549/241 |

FOREIGN PATENT DOCUMENTS 161368  9/1984  Japan .................................. 549/242

OTHER PUBLICATIONS

Francis, Chem. Abst. 68-30419q (1968).
Schulz et al, Chem. Abst. 93-133057r (1980).
Evans et al, Chem Abst 101-38948g (1984).
Mitsubishi Electric Corp., Chem. Abst 102-195193y (1985).
Schwartz, Chem Abst. 111-173974j (1989).
Molinaro et al, Chem. Abst. 112-98366c (1990).
International Business Machines Corp., Chem. 104-69623p (1986).
Uno et al, Chem. Abst. 105-79946 f (1986).
Pfeifer et al, Chem. Abst. 106-177090n (1987).
Scola et al, Chem. Abst. 106-197313r (1987).

*Primary Examiner*—Cecilia Shen
*Attorney, Agent, or Firm*—Harry Falber

[57] ABSTRACT

Aromatic dianhydrides being substituted in the positions ortho to the bridging moiety, said substituent groups including halogen, alkyl, hydroxy, nitro, cyano, ester, alkoxy, perfluoroalkyl, mercapto and thioester groups, said dianhydrides providing certain beneficial properties to polyimides prepared therefrom.

6 Claims, No Drawings

DISUBSTITUTED AROMATIC DIANHYDRIDES

Tetracarboxylic acids and the esters, amides, halides and anhydrides thereof are well known to those skilled in the art, particularly in terms in their use in the preparation of polyimide systems. Thus, these materials are reacted with a variety of diamines to prepare the polyimides. The reaction generally proceeds by the formation of a polyamide acid intermediate which is then cyclized to the polyimide form. The polyimides are suitable for the production of films, protective coatings and photolithographic relief images.

A broad range of such acids and anhydrides are disclosed, for example, in U.S. Pat. No. 3,856,752, U.S. Pat. No. 4,629,777, U.S. Pat. No. 4,631,335 and U.S. Pat. No. 4,698,295. Benzophenonetetracarboxylic acid anhydrides are particularly preferred. In general, the positions ortho to the bridging moiety in the dianhydride configuration have been left unsubstituted, such substitution having been observed solely in the acid form (see U.S. Pat. No. 4,698,295). Broad generic references to such a substitution pattern are disclosed in U.S. Pat. No. 4,578,166. However, the substituents are identified solely by a floating bond in the aromatic ring and are not specifically exemplified in the disclosure.

Accordingly, it is a primary object of the invention to provide a class of substituted tetracarboxylic acid dianhydrides which impart a broad spectrum of improved properties to the polyimides prepared therefrom.

Other objects and advantages of this invention will become evident from the following description thereof.

It has now been surprisingly discovered by introducing substituents into the ortho positions relative to the bridging moiety of aromatic tetracarboxylic acid dianhydrides, a number of benefits are evidenced when said dianhydrides are utilized in the preparation of polyimides. Thus, such polymides exhibit increased solubility in a wide variety of solvents, good thermal stability, higher glass transition temperatures, reduced coefficients of thermal expansion, increased photospeed of the crosslinking reaction in negative photoresist systems and solubility advantages in terms of developers in positive photoresist systems. The indicated solubility allows the polyimides to be coated in the fully cyclized form further resulting in less shrinkage during subsequent curing, less stress on coated films, lower processing temperatures and greater ease and economy of shipment. Such benefits are noted relative to the corresponding use of unsubstituted dianhydride compounds. In addition, the use of the dianhydride form relative to the acid form allows for the imidization reaction to be conducted at temperatures ranging from $-20°$ C. to $30°$ C. rather than at elevated temperatures and to eliminate the formation of HCl which is obtained when proceeding through the acid chloride in the prior art procedures.

The dianhydrides of the invention correspond to the formula

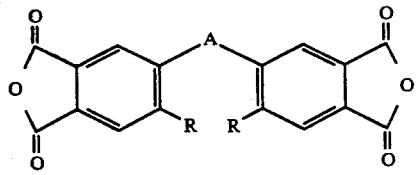

wherein A is a direct bond,

$-O-$, $-S-$, $-SO-$, $-SO_2-$, $C_1-C_3$ alkylene, $-C(CF_3)_2-$, $-CF_2-CF_2-$ or $-CHOH-$; and R is independently halogen, $C_1-C_6$ alkyl, OH, $OR_1$, $NO_2$, $COOR_1$, $CF_3$, $(CF_2)_{1-4}CF_3$, CN, SH or $SOR_1$ with $R_1$ being $C_1-C_6$ alkyl.

A is preferably the direct bond,

$-O-$, $-SO_2-$, $-CH_2-$, and most preferably

R is preferably halogen, methyl, ethyl, methoxy, and most preferably chlorine.

By way of illustration of the preparation of these compounds, the preferred dichloro benzophenone dianhydride is generally prepared by reacting the appropriate starting aromatic compound with oxalyl chloride in the presence of aluminum chloride to prepare the 2,2'-dichloro-4,4',5,5'-tetramethylbenzophenone. The resulting compound is then oxidized, preferably in the presence of nitric acid, to form the tetracarboxylic acid intermediate. Finally, the acid is dehydrated in aromatic solvents and at elevated temperatures or at elevated temperature alone ranging from 180° to 290° C. or by recrystallization from dehydrating agents such as acetic anhydride, to produce the dianhydride product.

More details regarding the preparation of specific anhydrides are disclosed in U.S. Pat. No. 4,698,295, these preparative procedures being incorporated herein.

It is to be noted that 2,2'-dichloro-4,4',5,5'-benzophenone tetracarboxylic dianhydride is preferred for purposes of this invention. Other applicable compounds are the corresponding diphenyl, diphenyl ether, diphenyl thioethers, sulfoxide, and sulfone compounds.

The preparation of polyimides utilizing the dianhydrides is advantageously carried out in solution. The reaction temperatures can be $-20°$ to $300°$ C. In detail, a procedure is advantageously followed in which the tetracarboxylic dianhydride and the diamine component are first reacted to form a polyamic acid precursor and this polyamic acid is then cyclized, water being detached. Cyclization can be carried out under the influence of heat. The cyclization is advantageously carried out under the influence of dehydrating agents, for example, carboxylic anhydrides, such as acetic anhydride. The polyimides can then be isolated by customary processes, for example by removal of the solvent or precipitation by addition of a non-solvent. The resulting polyimides can be used for the production of protective coatings, films and photolithographic relief images by techniques known in the art.

The following examples will further illustrate the embodiments of the instant invention. In these examples all parts given are by weight unless specifically indicated otherwise.

EXAMPLE 1

Synthesis of 2,2'-dichloro-4,4',5,5'-benzophenone tetracarboxylic dianhydride A flask fitted with mechanical stirrer, nitrogen inlet, thermometer, condenser and caustic filled HCl traps is charged with 4-chloro-o-xylene (560 g, 3.98 moles) and oxalyl chloride (272 g, 2.14 moles) which is washed with 2000 mls of $CS_2$. The reaction mixture is then cooled to 0° C. and aluminum chloride (584 g, 4.38 moles) is then added in eight equal portions over a 2 hour period. The reaction is warmed to room temperature and stirred for an additional 20 hours. The reaction mixture is then diluted with 800 mls of $CHCl_3$ and poured over ice with stirring whereupon the aluminum complex is filtered off. The organic layer is removed and the aqueous layer is then extracted with $4 \times 400$ mls of $CHCl_3$. The combined organic phase is then washed with $3 \times 500$ mls $H_2O$ and 500 mls of a saturated NaCl solution. The organic layer is dried over $MgSO_4$ and then concentrated under reduced pressure. The crude 2,2'-dichloro-4,4',5,5'-tetramethylbenzophenone is recrystallized from isopropyl ether in a ratio of 100 g of crude product to 2250 mls of isopropyl ether. The yield is 459 g (75%). Elemental Analysis: theory C: 66.46%, H: 5.25%, O: 5.21%, Cl: 23.08%; found C: 66.8%, H: 5.5%, O: 5.2%, Cl: 23.1%.

The 2,2'-dichloro-4,4',5,5'-tetramethylbenzophenone (20.4 g, 66.4 mmoles) is charged to a glass pressure flask and rinsed in with 500 mls of 20% $HNO_3$. The flask is then sealed with an all glass pressure relief valve and then placed in a titanium pressure reactor with 400 mls of water surrounding the flask. The reactor is then sealed and heated at 180° C. for 24 hours. The glass pressure flask is removed and cooled in an ice bath to precipitate the 2,2'-dichloro-4,4',5,5'-benzophenonetetracarboxylic acid product. The product is filtered and the residual $HNO_3$ is then removed by washing the solid with ice water. The yield is 17.3 g (85%). Elemental Analysis: theory C: 47.80%, H: 1.89%, O: 33.71%, Cl: 16.60%; found C: 48.19%, H: 2.12%, O: 33.45%, Cl: 16.14%.

A 2000 ml 3-neck flask fitted with mechanical stirrer, $N_2$ inlet, condenser, and Dean-Stark trap is charged with the 2,2'-dichloro-4,4',5,5'-benzophenonetetracarboxylic acid (222 g, 0.519 moles) and 1330 mls of a solvent composed of 73.5% phenyl ether and 26.5% biphenyl. The reaction mixture is heated to 230° C. and maintained for 8 hours under $N_2$. A dark brown solution results. Upon cooling to room temperature, the 2,2'-dichloro-4,4',5,5'-benzophenonetetracarboxylic dianhydride (DCBTDA) is precipitated. The product is filtered, washed with $CHCl_3$ and then recrystallized from acetic anhydride (1500 mls). The yield is 183 g (90%). $^{13}C$—NMR 191.0=(C=O), 162.1=, 162.3=(anh. C=O), 140.0=(C—Cl).

The difluoro-substituted dianhydride can be prepared in a comparable manner.

In summary, this invention is seen to provide a new class of disubstituted tetracarboxylic acid dianhydrides. Variations may be made in proportion, procedures and materials without departing from the scope of the claims as defined herein.

What is claimed is:

1. A compound of the formula

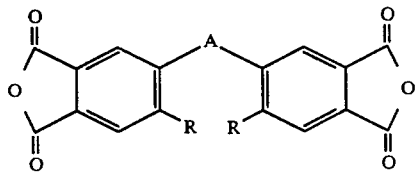

wherein
A is a direct bond,

—O—, —$SO_2$—, —$CH_2$—or —$C(CF_3)_2$—and
R is independently halogen, OH, $OR_1$, $NO_2$, $COOR_1$, $CF_3$ or $(CF_2)_{1-4}CF_3$ with $R_1$ being $C_1$–$C_6$alkyl.

2. The compound of claim 1 wherein A is the direct bond,

—O—, —$SO_2$—or —$CH_2$—.

3. The compound of claim 2, wherein A is

4. The compound of claim 1, wherein R is halogen or methoxy.

5. The compound of claim 4, wherein R is chlorine.

6. 2,2'-Dichloro-4,4',5,5'-benzophenone-tetracarboxylic acid dianhydride according to claim 1.

* * * * *